United States Patent [19]

Chau et al.

[11] Patent Number: 5,575,708
[45] Date of Patent: Nov. 19, 1996

[54] BELT GRINDING MACHINE AND METHOD FOR FORMING CUTTING EDGES ON SURGICAL INSTRUMENTS

[75] Inventors: Sonny Chau, Gurnee; Michael T. Dennehey, Arlington Heights, both of Ill.

[73] Assignee: Alligiance Corporation, McGaw Park, Ill.

[21] Appl. No.: 485,768

[22] Filed: Jun. 7, 1995

[51] Int. Cl.$^6$ ...................................................... B24B 21/00
[52] U.S. Cl. .............................. 451/305; 451/58; 451/45
[58] Field of Search ............................ 451/45, 296, 297, 451/355, 366, 380, 382, 387, 405, 214, 300, 305, 307, 40, 310, 304, 377, 264

[56] References Cited

U.S. PATENT DOCUMENTS

| | | | |
|---|---|---|---|
| 160,686 | 3/1875 | Kingman | 451/365 |
| 279,075 | 6/1883 | Berry | 451/58 |
| 2,215,752 | 9/1940 | Enya . | |
| 2,353,683 | 7/1944 | Martines | 451/59 |
| 2,525,264 | 10/1950 | Milner et al. | 451/382 |
| 2,802,310 | 8/1957 | Chaplik . | |
| 2,838,883 | 6/1958 | Hall | 451/382 |
| 3,539,314 | 11/1970 | Rockfeller et al. . | |
| 4,173,100 | 11/1979 | MacBroom . | |
| 4,216,628 | 8/1980 | Wada | 451/382 |
| 4,964,241 | 10/1990 | Conklin . | |
| 5,155,943 | 10/1992 | Matsutani et al. . | |
| 5,263,974 | 11/1993 | Matsutani et al. . | |
| 5,282,715 | 2/1994 | Abbate et al. . | |
| 5,388,373 | 2/1995 | Abbate et al. | 451/306 |

Primary Examiner—D. S. Meislin
Assistant Examiner—George Nguyen
Attorney, Agent, or Firm—John R. Flanagan; Robert A. Stenzel

[57] ABSTRACT

A belt grinding machine for forming cutting edges of complex geometry on surgical instruments includes a fixture for holding an instrument with a site thereon in a position for grinding a surface at the site on the instrument, a grinding assembly having a grinding belt with a planar span for grinding the surface at the site on the instrument, an oscillation producing mechanism for oscillating the instrument relative to the grinding belt so as to reciprocally translate the site on the instrument parallel and relative to the planar span of the grinding belt concurrently with grinding the surface at the site on the instrument, a translation producing mechanism for selectively translating the grinding assembly and thus the planar span of the grinding belt toward and away from the site on the instrument to permit receiving and setting up of the instrument in the instrument holding fixture and to place the instrument in a position for the planar span of the grinding belt to grind the surface at the site on the instrument, a grinding angle setting mechanism for selectively changing the angular relationship of the planar span of the grinding belt relative to the site on the instrument to grind another surface thereon, and a grinding site setting mechanism for rotating the instrument relative to the planar span of the grinding belt for selectively changing the location of the site on the instrument.

28 Claims, 8 Drawing Sheets

BELT GRINDING MACHINE AND METHOD FOR FORMING CUTTING EDGES ON SURGICAL INSTRUMENTS

BACKGROUND OF THE INVENTION

1. Field of the Invention

The present invention generally relates to techniques for manufacturing surgical instruments and, more particularly, is concerned with a belt grinding machine and method for forming cutting edges of complex geometry on surgical instruments.

2. Description of the Prior Art

Different surgical instruments, such as surgical needles, biopsy instruments and the like, have cutting edges of diverse and complex geometry formed thereon. These cutting edges need to be formed at particular angles which differ from one type of instrument to another depending on how the given instrument is used in the various surgical procedures.

One current approach to forming cutting edges on surgical needles requires the employment of two machines which use grinding wheels. Due to the limits of the grinding wheel contact surface, grinding material media and material removal rates, the tips of the needles are preliminarily ground on one machine and then passed to another machine to finish the grinding process. This is a cumbersome and time-consuming approach.

Other troublesome problems arise under the current approach. The grinding wheel traverses horizontally across the needle. The tight spacing from the needle tip of the structure supporting the needle tip limits the ability of the wheel to grind closely to the needle tip. Also, the grinding cycle time is lengthy, such as about five minutes. Further, the grinding wheel surface finish is restricted to one type of media which typically breaks down relatively fast. The wheel dressing procedure to restore the media, which is manually performed by an operator, is hazardous and time consuming, and involves a complicated grinding algorithm. Finally, as more needles are ground, the grinding wheel decreases in diameter. The feed rate must be changed accordingly to obtain a precisely finished needle.

Consequently, a need exists for a different approach to forming the cutting edges on surgical instruments, such as needles, which will overcome the aforementioned problems of the current grinding wheel technique without introducing a new set of problems in their place.

SUMMARY OF THE INVENTION

The present invention provides a belt grinding machine and method for forming cutting edges of complex geometry on surgical instruments, such as needles, in a manner which meets the aforementioned need. The belt grinding approach has several advantages over the prior art wheel grinding approach. First, a multiple insert fixture of the belt grinding machine for holding the instruments to be ground accommodates larger scales of instruments in different lengths, gauges and plastic molded hubs. Second, grinding belt abrasive cutting provides much more precision and removes material at larger rates. For instance, about ¼ inch stock can be removed at three seconds. Third, different kinds of grinding can be used to achieve selected surface finishes on the instruments. Fourth, the grinding belt will last longer, for example, through approximately 500 needles. Also, the grinding belt can be replaced quickly, such as within a few minutes. Fifth, the grinding belt thickness is about 2 mils. Thus, the needle contact position is very precise. Sixth, the site of grinding can be protected by an enclosure and a filter to prevent mists carrying grinding powders to escape and contaminate the atmosphere. Seventh, the belt grinding operation is inherently a high-speed operation, with the grinding belt making 25 revolutions past the support platen per second. The grinding belt rides upon a support platen generating extreme heat underneath the belt requiring cooling which, in turn, requires precise dispensing of coolant at each location of grinding on the needle. Eighth, cooling and keeping the grinds out of the mechanical components reduces wear and tear on the grinding machine. Ninth, components of the grinding machine of the invention have multiple axes allowing the making of various multiple adjustments which contributes to the overall enhanced precision of the belt grinding machine.

Accordingly, the present invention is directed to a belt grinding machine for forming cutting edges of complex geometry on surgical instruments. The belt grinding machine comprises: (a) a support frame; (b) a fixture mounted on the support frame for holding at least one instrument with a predetermined site thereon in a preset position for grinding a predetermined surface at the predetermined site thereon; (c) a grinding assembly mounted on the support frame and including a movable grinding belt with a planar span for grinding the predetermined surface at the predetermined site on the instrument; and (d) an oscillation producing mechanism mounted on the support frame and coupled to the fixture and being operable to oscillate the instrument relative the grinding belt to reciprocally translate the predetermined site on the instrument substantially parallel and relative to the planar span of the grinding belt driving grinding of the predetermined surface at the predetermined site on the instrument by the movable grinding belt.

The belt grinding machine of the present invention further comprises: (e) a translation producing mechanism mounted on the support frame and supporting the grinding assembly and being operable to selectively translate the grinding assembly and thus the planar span of the grinding belt toward and away from the predetermined site on the instrument to permit receiving and setting up of the instrument in the fixture and to place the instrument in a position for the planar span of the grinding belt to grind the predetermined surface at the predetermined site on the instrument; (f) a grinding angle setting mechanism mounted on the support frame and coupled to the grinding assembly and being operable to selectively change the angular relationship of the planar span of the grinding belt relative to the predetermined site on the instrument to grind another predetermined surface thereon; and (g) a grinding site setting mechanism mounted on the support frame and coupled to the instrument and being operable to rotate the instrument relative to the grinding belt and thus the planar span of the grinding belt to selectively change the location of the predetermined site on the instrument.

The present invention also is directed to a belt grinding method for forming cutting edges of complex geometry on surgical instruments. The belt grinding method comprises the steps of: (a) holding at least one instrument with a predetermined site thereon in a preset position for grinding a predetermined surface at the predetermined site thereon; (b) operating a grinding belt having a planar span to grind the predetermined surface at the predetermined site on the instrument; and (c) oscillating the instrument and thus the predetermined site thereon substantially parallel and relative to the planar span of the grinding belt during grinding the predetermined surface at the predetermined site on the instrument.

The belt grinding method of the present invention further comprises the steps of: (d) selectively translating the grinding belt and thus the planar span therewith toward and away from the predetermined site on the instrument to permit receiving and setting up of the instrument in an instrument holding fixture and to place the instrument in a position for the planar span of the grinding belt to grind the predetermined surface at the predetermined site on the instrument; (e) selectively changing the angular relationship of the planar span of the grinding belt relative to the predetermined site on the instrument to grind another predetermined surface thereon; and (f) rotating the instrument relative to the planar span of the grinding belt for selectively changing the location of the predetermined site on the instrument.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which.

DETAILED DESCRIPTION OF THE INVENTION

Figure 1:
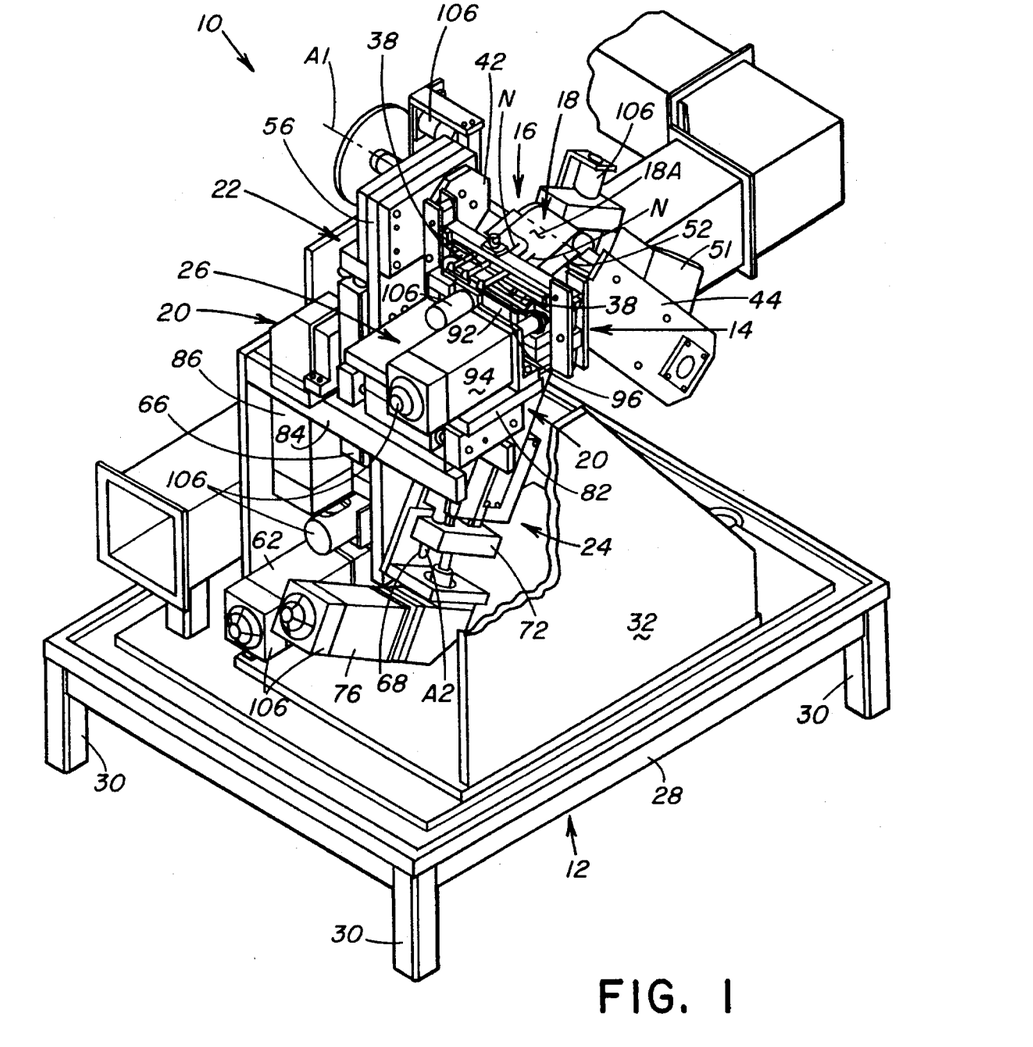
FIG. 1 is a perspective view of a belt grinding machine of the present invention for forming cutting edges on surgical instruments.
Figure 2:
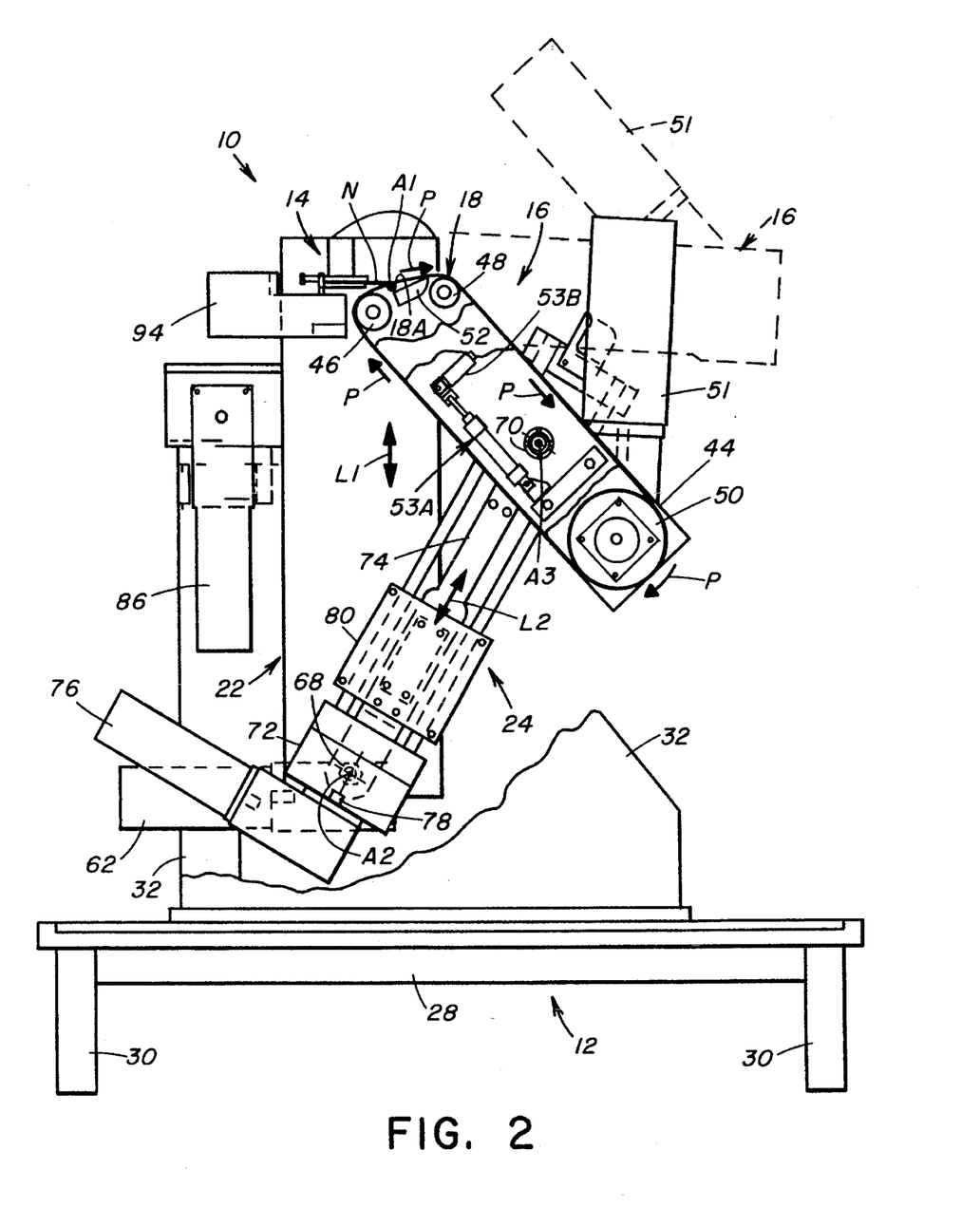
FIG. 2 is an enlarged side elevational view of the machine of FIG. 1.
Figure 3:
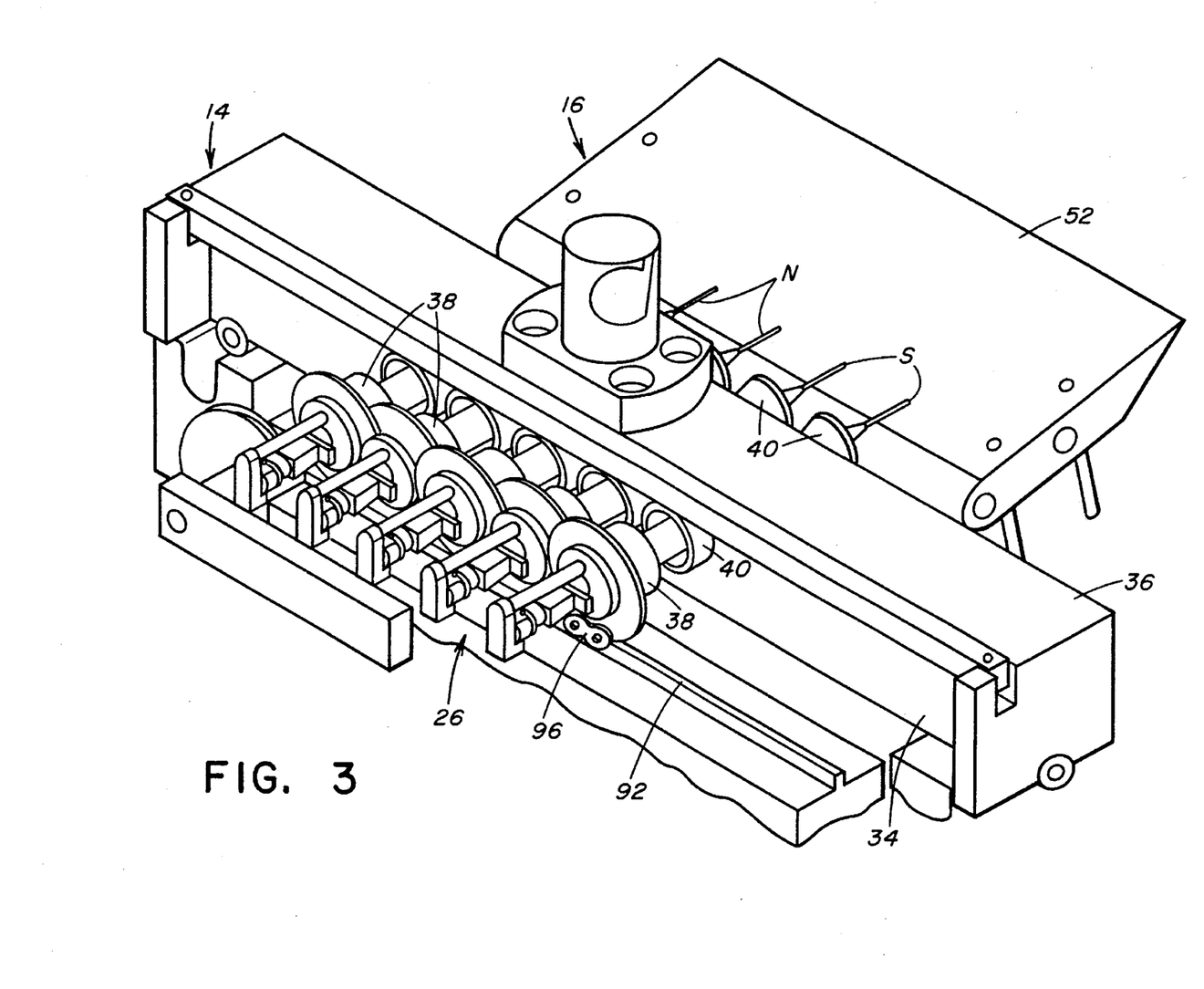
FIG. 3 is an enlarged fragmentary perspective view of a needle holding fixture and a belt support platen of the machine of FIG. 1.
Figures 4, 5, 6A, 6B, 7:
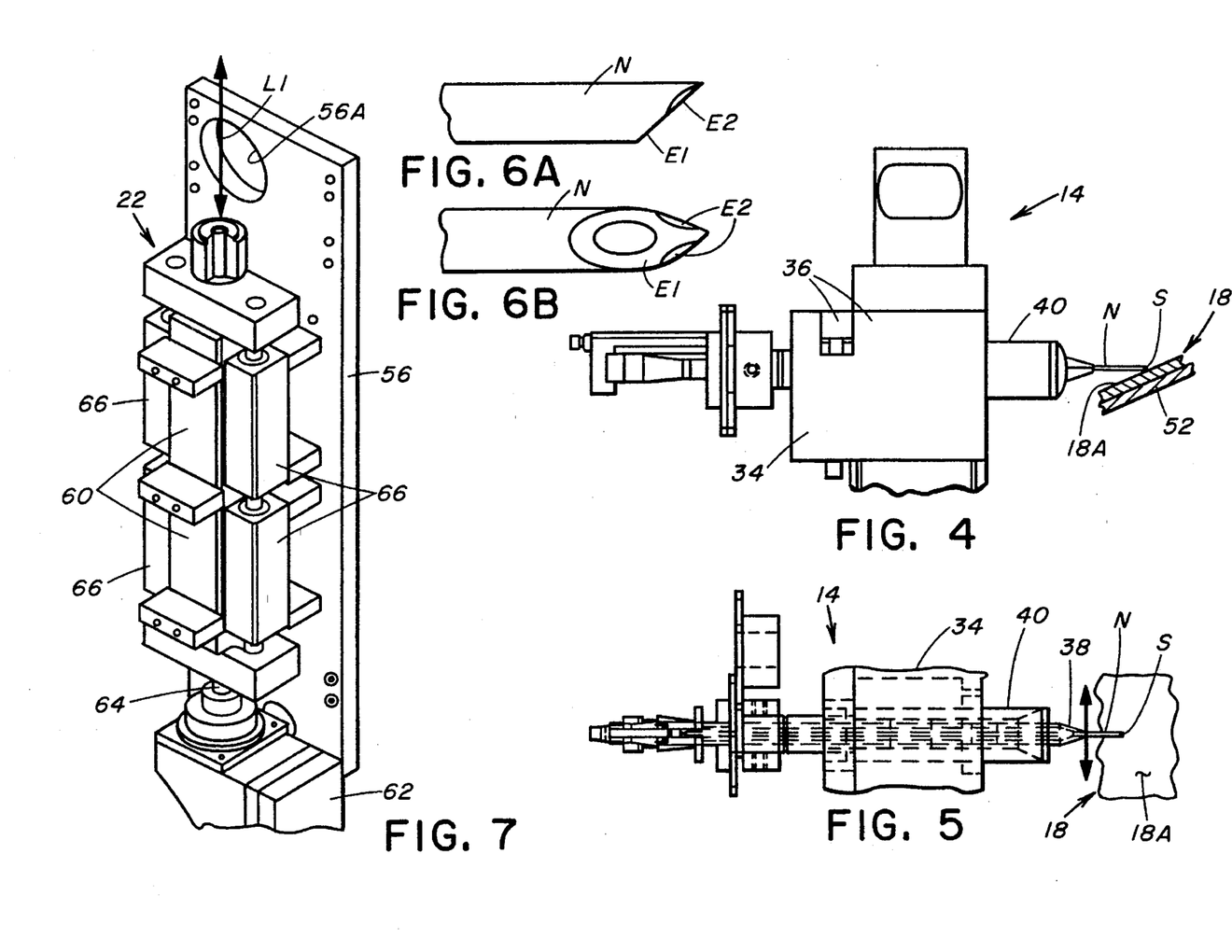
FIG. 4 is a right end elevational view of the needle holding fixture of FIG. 3.
FIG. 5 is a top plan view of the needle holding fixture of FIG. 4.
FIG. 6A is an enlarged fragmentary side elevational view of a tip of a surgical needle having a cutting edge formed thereon.
FIG. 6B is an enlarged top plan view of the tip of the needle showing the cutting edges ground thereon.
FIG. 7 is an enlarged fragmentary perspective view of a belt elevating mechanism of the machine of FIG. 1.

Referring to the drawings, and particularly to FIGS. 1–3, there is illustrated a belt grinding machine of the present invention, generally designated 10, for forming cutting edges E1, E2 of complex geometry on surgical instruments, such as a needle N, as seen in FIGS. 6A and 6B. Although the belt grinding machine 10 is adaptable for grinding cutting edges on different surgical instruments, the machine 10 will be described hereinafter in application to surgical needles N. It should be understood, however, that the term "needle" or "needles" is being used hereinafter for sake of brevity and not by way of limitation of the present invention.

Referring now to FIGS. 1 and 2, the belt grinding machine 10 basically includes a main support frame 12, an instrument holding fixture 14, and a grinding assembly 16. The fixture 14 is supported on the support frame 12 and adapted to receive and hold at least one and preferably a plurality of needles N, each having a predetermined site S identified thereon, typically the tip of the needle N, at which it is desired to grind a surface having a predetermined geometry, such as the cutting edges shown in FIGS. 6A and 6B. The grinding assembly 16 is supported on the support frame 12 and includes a movable endless grinding belt 18 having a generally planar extending span 18A for grinding the surface of the desired geometry at the predetermined site S on the needle N. The belt grinding machine 10 also includes an oscillation producing mechanism 20, a translation producing mechanism 22, a grinding angle setting mechanism 24, and a grinding site setting mechanism 26.

Referring still to FIGS. 1 and 2, the support frame 12 of the machine 10 includes a large rectangular platform 28 having legs 30 rigidly attached thereto and extending downwardly from the four corners of the platform 28 to a support surface. The support frame 12 also includes a rectangular superstructure 32 attached upon the platform 28 and extending thereabove. The support frame 12 described above is by way of example only, there being many other likely configurations within the purview of the present invention.

Referring to FIGS. 1–5, the instrument holding fixture 14 of the machine 10 includes a base 34 supported by the superstructure 32 of the support frame 12 and an elongated holder cover 36 releasably and removably secured upon the base 34. The fixture 14 also includes a plurality of needle insert holders 38 which each hold one of the needles N and is, in turn, rotatably supported through a tubular element 40 mounted on the fixture base 34.

Figure 9:
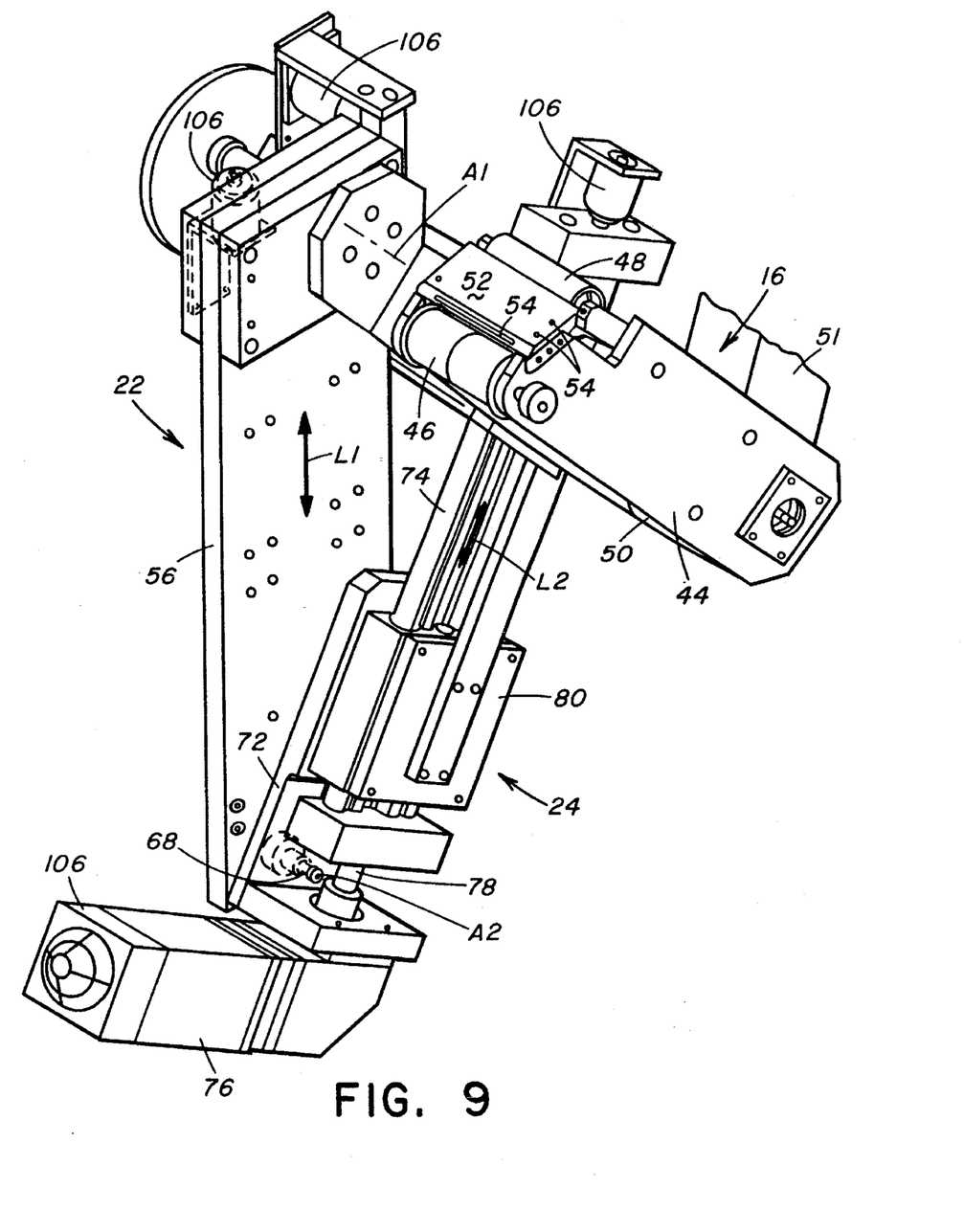
FIG. 9 is an enlarged fragmentary perspective view of a belt angle adjusting mechanism of the machine of FIG. 1.
Figures 10, 11:
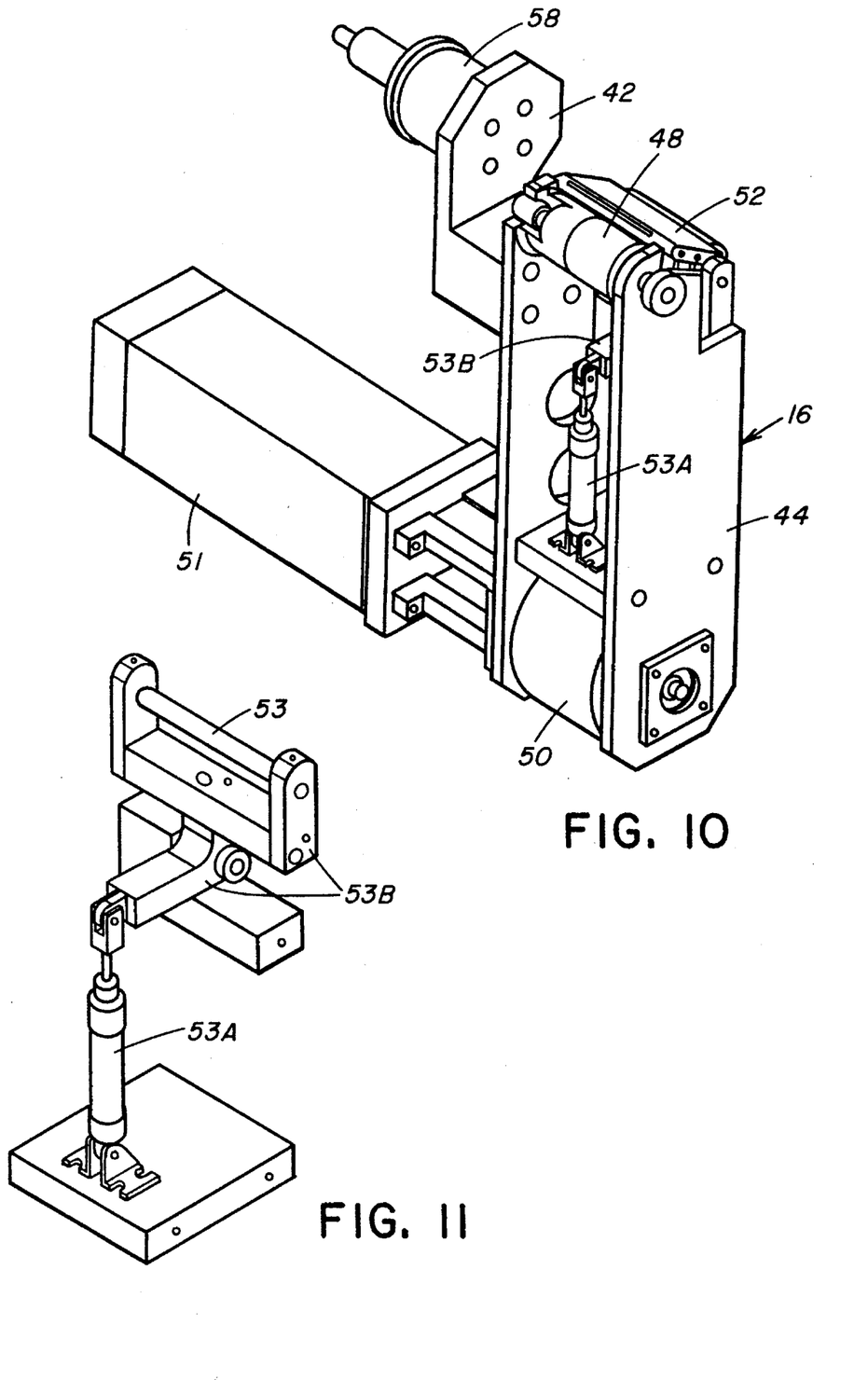
FIG. 10 is an enlarged fragmentary perspective of a belt speed control mechanism of the machine of FIG. 1.
FIG. 11 is an enlarged perspective of a belt tension control mechanism of FIG. 10.

Referring to FIGS. 1–3 and 9–11, the grinding assembly 16 of the machine 10 includes a support member 42 mounted for undergoing pivotal movement about an upper first pivot axis A1 aligned with the predetermined sites S on the respective needles N and an auxiliary frame 44 mounted to the support member 42 and including a pair of upper spaced apart idler rollers 46, 48 and a lower drive roller 50 over and between which the grinding belt 18 is entrained and supported for movement about an endless path. The grinding assembly 16 also includes a belt support platen 52 mounted to the auxiliary frame 44 between the upper idler rollers 46, 48 and adjacent to the instrument holding fixture 14. The belt support platen 52 is disposed along the endless path of movement of the grinding belt 18 and underlies the grinding belt 18 so as to support the short span thereof extending between the upper idler rollers 46, 48 and along the front of the fixture 14 in a substantially planar orientation. This short span thus is the aforementioned planar span 18A of the grinding belt 18 which is engaged by the needles N and intersects the upper first pivotal axis A1 of the grinding assembly 16 and thus is in a preset position to grind the predetermined surface at the predetermined sites S on the respective needles N. The grinding assembly 16 further includes belt drive means in the form of a first servo motor 51 (also identified as M1 in FIG. 12) mounted to the auxiliary frame 44 and drivingly engaged with the lower drive roller 50 and thus drivingly coupled with the grinding belt 18 to rotatably drive the grinding belt 18 about the endless path in the direction of arrow P. As seen in FIGS. 2, 10 and 11, a belt tensioning means formed by an actuator 53A and a pivotally mounted crank yoke 53B are pivotally coupled to one another and pivotally mounted to the auxiliary frame 44 for moving the upper idler roller 48 to apply the desired tension to the grinding belt 18. The roller 48 is rotatably mounted to an axle 53C on the yoke 53B.

Also, the belt support platen 52 contains passages 54 therethrough which receive a suitable grinding coolant solution circulated from a tank (not shown) by operation of a sump pump (not shown) in the tank. The coolant solution is pumped through a common line, then tees off into two different paths. One path goes through the needle fixture 14 above the tips of the needles N; the second path goes through the support platen 52 and is dispensed through several holes on the platen. Suitable means (not shown) is provided for collecting the coolant solution leaving the platen 52.

Referring to FIGS. 1, 2, 7 and 9, the translation producing mechanism 22 of the machine 10 is mounted on the superstructure 32 of the main support frame 12 and supports the grinding assembly 16. The translation producing mechanism 22 is operable selectively to move or translate the grinding assembly 16 along a first substantially vertical translatory path or axis in the direction of the double headed arrow L1 in FIGS. 2, 7 and 9, extending in orthogonal relation to the upper first pivot axis A1 and thereby to translate the planar span 18A of the grinding belt 18 toward and away from the predetermined sites S on the respective needles N. Thus, the translation producing mechanism 20 will initially be operated to move the grinding assembly 16 downwardly away from the position where the needles N will be installed so as to permit receiving and setting up of the needles N in the fixture 14. Once the needles N are placed in the desired position for the planar span 18A of the grinding belt 18 to grind the predetermined surfaces thereon, the translation producing mechanism 20 will then be operated to move the grinding assembly 16 upwardly into contact with the predetermined grinding sites S on the respective needles N where grinding of the predetermined surfaces thereon is to occur.

More particularly, the translation producing mechanism 22 includes a first supplementary frame member 56 having an opening 56A through its upper end whose center is coincident with the upper first pivotal axis A1. A hub element 58 on the support member 42 of the grinding assembly 16 extends through the opening 56A so as to be rotatably supported by the first supplementary frame member 56 so that the grinding assembly 16 can undergo pivotal movement about the upper first pivotal axis A1. The translation producing mechanism 22 also includes a second supplementary frame member 60 which is mounted to the superstructure 32 of the main support frame 12 and, in turn, supports the first supplementary frame member 56 for undergoing linear or translatory movement relative to the superstructure 32 of the support frame 12 along the substantially vertical first translatory axis L1 extending in orthogonal relation to the upper first pivotal axis A1.

The translation producing mechanism 22 further includes a translatory drive means in the form of a second servo motor 62 (also identified as M2 in FIG. 12) mounted to superstructure 32 of the support frame 12 and interengaged with the first supplementary frame member 56 via a threaded rotary drive screw 64 connected to and driven by the second servo motor 62 and a slide structure 66 threaded with the drive screw 64 and attached to the first supplementary frame member 56. The second servo motor 62 is operable to selectively drive movement of the first supplementary frame member 56 along the first translatory axis L1 and thereby translate the grinding assembly 16 and thus the planar span 18A of the grinding belt 18 therewith toward and away from the predetermined sites S on the respective needles N as described earlier.

Referring to FIGS. 1, 2 and 9, the grinding angle setting mechanism 24 of the machine 10 is mounted on the support frame 12 via a lower pivotal connection 68 to the translation producing mechanism 22. The angle setting mechanism 24 also is coupled to the grinding assembly 16 via an upper pivotal connection 70 and is operable to selectively pivot the grinding assembly 16 about the upper first pivot axis A1 and thereby change the angular relationship of the planar span 18A of the grinding belt 18 relative to the predetermined site S on the needles N to grind different selected predetermined surface thereon. Particularly, the grinding angle setting mechanism 24 includes a first auxiliary support member 72 connected at the lower pivotal connection 68 to the first supplementary frame member 56 of the translation producing mechanism 22 for undergoing pivotal movement relative thereto about a lower second pivot axis A2 defined by the lower pivotal connection 68 and spaced from and aligned parallel with the upper first pivot axis A1. The angle setting mechanism 24 also includes a second auxiliary support member 74 connected at the upper pivotal connection 70 to the auxiliary frame 44 of the grinding assembly 16 for undergoing pivotal movement about an upper third pivot axis A3 defined by the upper pivotal connection 70 and spaced from and aligned parallel with the lower second pivot axis A2 and the upper first pivot axis A1.

The angle setting mechanism 24 further includes a translatory drive means in the form of a third servo motor 76 (also identified as M3 in FIG. 12) mounted to the first auxiliary support member 72 and interengaged with the second auxiliary support member 74 via a threaded rotary drive screw 78 connected to and driven by the third servo motor 76 and a slide structure 80 threaded with the drive screw 78 and attached to the second auxiliary support member 74. The third servo motor 76 is operable to selectively drive movement of the second auxiliary support member 74 along a second translation axis L2 and thereby translate the second auxiliary support member 74 toward and away from the first auxiliary support member 72 to selectively pivotally move the grinding assembly 16 relative thereto to thereby change the angular relationship of the planar span 18A of the grinding belt 18 about the upper first pivot axis A1 and relative to the predetermined sites S on the respective needles N.

Referring to FIGS. 1–3 and 8, the oscillation producing mechanism 20 of the machine 10 is mounted on the superstructure 32 of the support frame 12 and is coupled to the fixture base 34 and operable to oscillate the fixture 14 and the needles N held therein relative to the grinding belt 18 of the grinding assembly 16 so as to reciprocally translate the predetermined sites S on the respective needles N substantially parallel and relative to the planar span 18A of the grinding belt 18 concurrently with grinding the desired surfaces at the sites S on the respective needles N. In such manner, the wear effects of the grinding operation on the grinding belt 18 are distributed equally across width of the moving belt 18.

Figure 8:
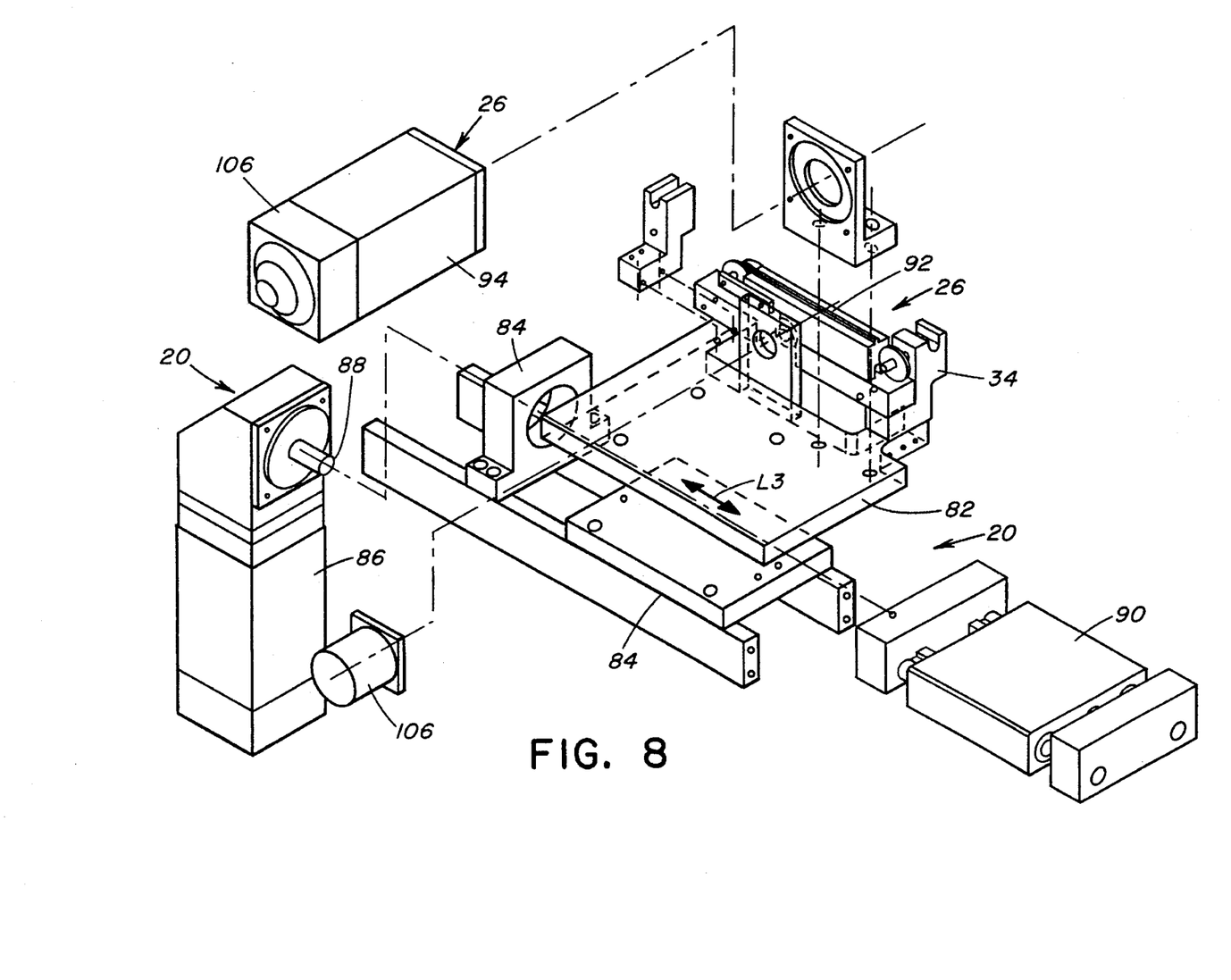
FIG. 8 is an enlarged exploded view of needle rotating and oscillating mechanism of the machine of FIG. 1.

More particularly, the oscillation producing mechanism 20 includes an auxiliary frame member 82 supporting the fixture 14 and a secondary support member 84 mounted to the superstructure 32 of the support frame 12 and supporting the auxiliary frame member 82 and thus the fixture 14 therewith for undergoing translatory movement relative to the support frame 12 along a third translation axis L3 extending substantially parallel to the upper first pivot axis A1 and to the planar span 18A of the grinding belt 18. The oscillation producing mechanism 20 further includes drive means in the form of a fourth servo motor 86 (also identified as M4 in FIG. 12) mounted to the secondary support member 84 and interengaged with the auxiliary frame member 82 via a threaded rotary drive screw 88 connected to and driven by the fourth servo motor 86 and a slide structure 90 threaded with the drive screw 88 and attached to the auxiliary frame member 82. The fourth servo motor 86 is operable to selectively drive movement of the the auxiliary frame member 82 and thereby reciprocally translate the fixture 14 and the needles N therewith. Concurrently, the grinding sites S of the respective needles N are moved in the oscillatory manner engaged with and substantially parallel and relative to the planar span 18A of the grinding belt 18.

Finally, the grinding site setting mechanism 26 of the machine 10 is mounted upon the auxiliary frame member 82 of the oscillation producing mechanism 20 and coupled with the needle insert holders 38 for rotating the holders 38 and the needles N therewith relative to the fixture 14 and also relative to the planar span 18A of the grinding belt 18 for selectively changing the location of the predetermined sites S on the respective needles N. The site setting mechanism 26 includes a guide track 92 supported on the auxiliary frame member 82 adjacent to the fixture 14 which is also supported thereon, a rotary drive means in the form of a fifth servo motor 94 for generating rotary motion, and movable means in the form of a flexible motion transitting member 96, such as an endless flexible chain, supported about and along the guide track 92 and drivingly interconnecting the fifth servo motor 94 with the needle insert holders 38 and thereby with the needles N therein. The fifth servo motor 94 is operable to move the motion transmitting member 96 along an endless path to selectively rotate the holders 38 and needles N therewith relative to the fixture 14 and to the planar span 18A of the grinding belt 18 to thereby selectively change the predetermined sites S on the respective needles N where the grinding of the predetermined surfaces thereon is to occur.

Figure 12:
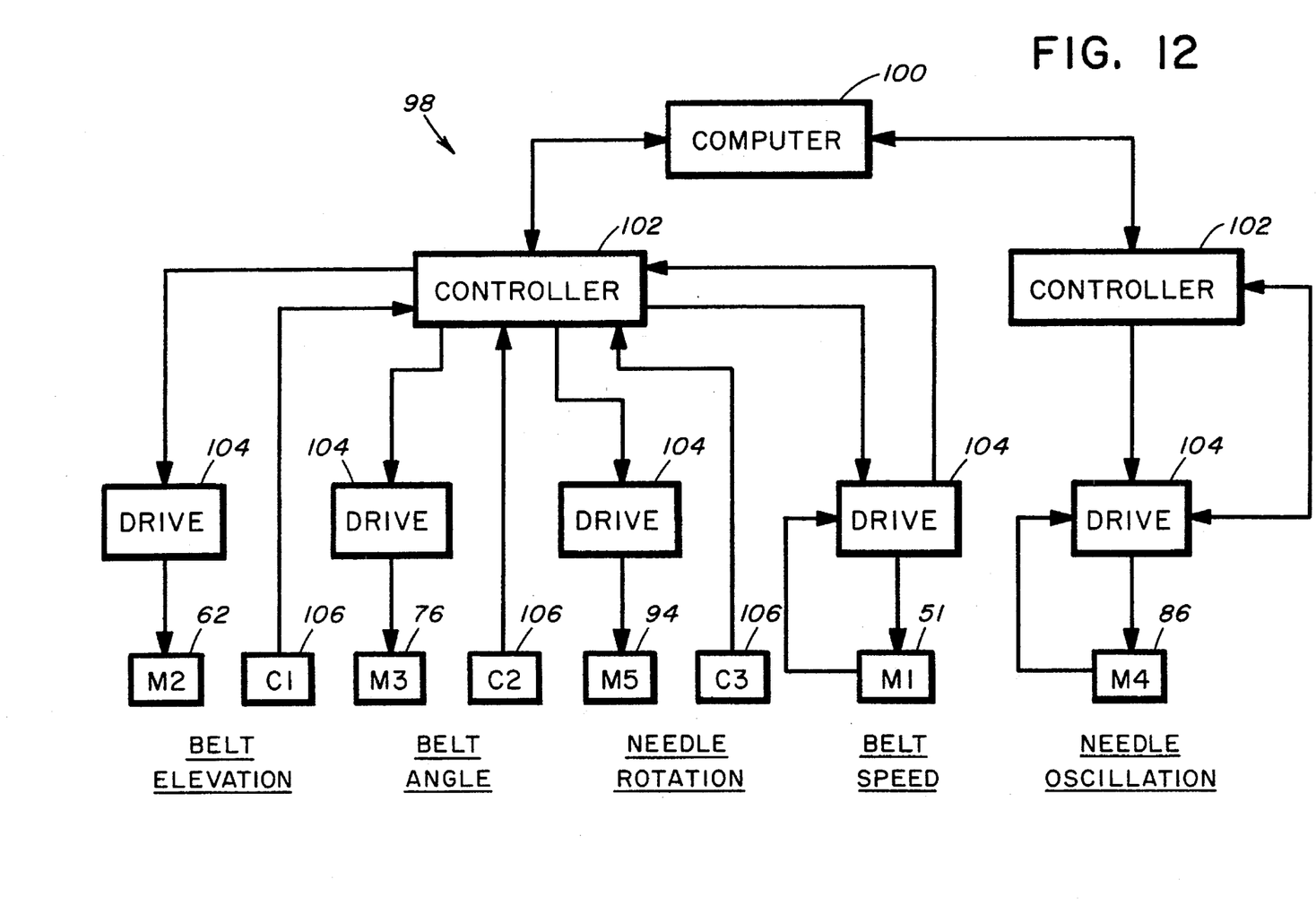
FIG. 12 is a block diagram of the arrangement of the motion controls of the belt grinding machine.

The above-described belt grinding machine 10 of the present invention thus can be understood to incorporate a closed-loop servo system employing multiple axes and data acquisition techniques which permit precise monitoring and control of operations so as to allow achievement of highly precise surfaces of complex geometries on the needles, such a shown in FIGS. 6A and 6B. The block diagram of FIG. 12 shows the overall general arrangement 98 of the motion controls employed by the belt grinding machine 10 for facilitating these objectives. In addition to the first through fifth servo motors 51, 62, 76, 86 and 94 described above, this arrangement 98 also includes a computer 100, controllers 102, a plurality of drives 104 as well as encoders 106 (some of which also identified as C1 to C3 in FIG. 12) to achieve the close monitoring and control functions. The computer and controllers 100, 102 provide the memory and processing capabilities necessary to store the parameters of and execute the instructions for forming all the various geometries of surfaces that are desired to be ground on the needles N. The drives 104 responding to the instructions accelerate and decelerate the servo motors at the correct rates to impart the correct motions to the various components of the mechanism described above. Finally, the encoders 106 sense the motion of the servo motors and the movements of the mechanisms described above and feedback this information to the controllers 102 to constantly monitor the orientation and position of the sites S on the needles N relative to the planar span 18A of the grinding belt 18 so as to ensure that the geometry of the actual surfaces ground on the needles N will conform precisely to those intended. This monitoring ensures that corrective action can be taken so as to maintain accuracy or that the machine 10 can be shut down to interrupt operations so that necessary corrective action can be implemented.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

We claim:

1. A belt grinding machine for forming cutting edges of complex geometry on surgical instruments, said machine comprising:

(a) a support frame;

(b) a fixture mounted on said support frame for holding at least one instrument with a predetermined site thereon in a preset position for grinding a predetermined surface at the predetermined site thereon;

(c) a grinding assembly mounted on said support frame and including a movable grinding belt having a planar span for grinding the predetermined surface at the predetermined site on the instrument;

(d) an oscillation producing mechanism mounted on said support frame and coupled to said fixture for oscillating said fixture and the instrument therewith relative to said grinding belt to reciprocally translate the predetermined site on the instrument substantially parallel and relative to said planar span of said grinding belt during said grinding of the predetermined surface at the predetermined site on the instrument by said movable grinding belt; and (e) a translation producing mechanism mounted on said support frame and supporting said grinding assembly and being operable to selectively translate said grinding assembly and thus said planar span of said grinding belt toward and away from the predetermined site on the instrument to permit receiving and setting up of the instrument in said fixture and to place the instrument in a position for said planar span of said grinding belt to grind the predetermined surface at the predetermined site on the instrument.

2. The machine of claim 1 wherein said oscillation producing mechanism includes:

an auxiliary frame member supporting said fixture;

a support member mounted to said support frame and supporting said auxiliary frame member and thus said fixture therewith for undergoing translatory movement relative to said support frame along an axis extending substantially parallel to said planar span of said grinding belt; and drive means mounted to said support member and engaged with said auxiliary frame member for selectively driving said auxiliary frame member to reciprocally translate said fixture and thereby the predetermined site of the instrument held in said fixture in an oscillatory manner substantially parallel and relative to said planar span of said grinding belt.

3. The machine of claim 1 further comprising:

(f) a grinding angle setting mechanism mounted on said support frame and coupled to said grinding assembly and being operable to pivotally move said grinding assembly about a first pivot axis and thereby selectively change the angular relationship of said planar span of said grinding belt relative to the predetermined site on the instrument to grind another predetermined surface thereon.

4. The machine of claim 1 further comprising:

(f) a grinding site setting mechanism mounted on said support frame and coupled to the instrument and being operable to rotate the instrument relative to said fixture and to said planar span of said grinding belt to selectively change the location of the predetermined site on the instrument.

5. A belt grinding machine for forming cutting edges of complex geometry on surgical instruments, said machine comprising:

(a) a support frame;

(b) a fixture mounted on said support frame for holding at least one instrument with a predetermined site thereon in a preset position for grinding a predetermined surface at the predetermined site thereon;

(c) a grinding assembly mounted on said support frame and including a movable grinding belt having a planar span for grinding the predetermined surface at the predetermined site on the instrument; and (d) a translation producing mechanism mounted on said support frame and supporting said grinding assembly and being operable to selectively translate said grinding assembly and thus said planar span of said grinding belt toward and away from the predetermined site on the instrument to permit receiving and setting up of the instrument in said fixture and to place the instrument in a position for said planar span of said grinding belt to grind the predetermined surface at the predetermined site on the instrument.

6. The machine of claim 5 wherein said grinding assembly includes:

a support member mounted for undergoing pivotal movement about a pivot axis aligned with the preset position;

an auxiliary frame mounted to said support member and supporting said grinding belt for movement about an endless path;

a belt support platen mounted to said auxiliary frame adjacent to said fixture and along said endless path underlying said grinding belt so as to support a short section thereof extending along said fixture and engaged by the instrument in a planar orientation defining said planar span of said grinding belt intersecting said first pivot axis of said support member and said preset position to grind the predetermined surface at the predetermined site on the instrument; and belt drive means mounted to said auxiliary frame and drivingly engaged with said grinding belt for driving said grinding belt about said endless path.

7. The machine of claim 6 wherein said translation producing mechanism includes:

a first supplementary frame member supporting said support member of said grinding assembly for undergoing pivotal movement about said pivot axis aligned with the preset position;

a second supplementary frame member mounted to said support frame and supporting said first supplementary frame member for undergoing translatory movement relative to said support frame along a translatory axis extending in orthogonal relation to said pivot axis; and translatory drive means mounted to said support frame and engaged with said first supplementary frame member and for selectively driving said first supplementary frame member along said translatory axis and thereby translating said grinding assembly and said planar span of said grinding belt therewith toward and away from the predetermined site on the instrument.

8. The machine of claim 5 further comprising:

(e) a grinding angle setting mechanism mounted on said support frame and coupled to said grinding assembly and being operable to pivotally move said grinding assembly about a first pivot axis and thereby selectively change the angular relationship of said planar span of said grinding belt relative to the predetermined site on the instrument to grind another predetermined surface thereon.

9. The machine of claim 5 further comprising:

(e) a grinding site setting mechanism mounted on said support frame and coupled to the instrument and being operable to rotate the instrument relative to said fixture and to said planar span of said grinding belt to selectively change the location of the predetermined site on the instrument.

10. A belt grinding machine for forming cutting edges of complex geometry on surgical instruments, said machine comprising:

(a) a support frame;

(b) a fixture mounted on said support frame for holding at least one instrument with a predetermined site thereon in a preset position for grinding a predetermined surface at the predetermined site thereon;

(c) a grinding assembly mounted on said support frame and including a movable grinding belt having a planar span for grinding the predetermined surface at the predetermined site on the instrument; and (d) a grinding angle setting mechanism mounted on said support frame and coupled to said grinding assembly and being operable to selectively pivotally move said grinding assembly about a first pivot axis and thereby change the angular relationship of said planar span of said grinding belt relative to the predetermined site on the instrument to grind another predetermined surface thereon, said grinding angle setting mechanism including (i) a first auxiliary support member supported by said support frame for undergoing pivotal movement relative thereto about a lower axis spaced from and aligned parallel with said first pivot axis, (ii) a second auxiliary support member connected to said grinding assembly for undergoing pivotal movement about an upper axis spaced from and aligned parallel with said lower and pivot axes, and (iii) drive means mounted to said first auxiliary support member and engaged with said second auxiliary support member for selectively driving said second auxiliary support member along a translation axis to thereby translate said second auxiliary support member toward and away from said first auxiliary support member and thereby selectively change the angular relationship of said planar span of said grinding belt relative to the predetermined site on the instrument.

11. The machine of claim 10 further comprising:

(e) a grinding site setting mechanism mounted on said support frame and coupled to the instrument and being operable to rotate the instrument relative to said fixture and to said planar span of said grinding belt to selectively change the location of the predetermined site on the instrument.

12. The machine of claim 11 further comprising:

(f) an oscillation producing mechanism mounted on said support frame and coupled to said fixture and being operable to oscillate said fixture and the instrument therewith relative to said grinding belt to reciprocally translate the predetermined site on the instrument substantially parallel and relative to said planar span of said grinding belt during said grinding of the predetermined surface at the predetermined site on the instrument by said movable grinding belt.

13. A belt grinding machine for forming cutting edges of complex geometry on surgical instruments, said machine comprising:

(a) a support frame;

(b) a fixture mounted on said support frame for holding at least one instrument with a predetermined site thereon in a preset position for grinding a predetermined surface at the predetermined site thereon;

(c) a grinding assembly mounted on said support frame and including a movable grinding belt having a planar span for grinding the predetermined surface at the predetermined site on the instrument;

(d) a grinding angle setting mechanism mounted on said support frame and coupled to said grinding assembly and being operable to selectively pivotally move said grinding assembly about a first pivot axis and thereby change the angular relationship of said planar span of said grinding belt relative to the predetermined site on the instrument to grind another predetermined surface thereon;

(e) a grinding site setting mechanism mounted on said support frame and coupled to the instrument and being operable to rotate the instrument relative to said fixture and to said planar span of said grinding belt to selectively change the location of the predetermined site on the instrument; and (f) a translation producing mechanism mounted on said support frame and supporting said grinding assembly and being operable to selectively translate said grinding assembly and thus said planar span of said grinding belt toward and away from the predetermined site on the instrument to permit receiving and setting up of the instrument in said fixture and to place the instrument in a position for said planar span of said grinding belt to grind the predetermined surface at the predetermined site on the instrument.

14. A belt grinding machine for forming cutting edges of complex geometry on surgical instruments, said machine comprising:

(a) a support frame;

(b) a fixture mounted on said support frame for holding at least one instrument with a predetermined site thereon in a preset position for grinding a predetermined surface at the predetermined site thereon;

(c) a grinding assembly mounted on said support frame and including a movable grinding belt having a planar span for grinding the predetermined surface at the predetermined site on the instrument; and (d) a grinding site setting mechanism mounted on said support frame and coupled to the instrument and being operable to rotate the instrument relative to said fixture and to said planar span of said grinding belt to selectively change the location of the predetermined site on the instrument, said grinding site setting mechanism including (i) a guide track supported by said support frame adjacent to said fixture, (ii) rotary drive means for generating rotary motion, and (iii) movable means supported by said guide track adjacent to said fixture and said instrument held by said fixture, said movable means interconnecting said rotary drive means with the instrument for selectively rotating the instrument relative to said fixture and said planar span of said grinding belt to thereby selectively change the predetermined site on the instrument for grinding a predetermined surface at the predetermined site thereon.

15. A belt grinding machine for forming cutting edges of complex geometry on surgical instruments, said machine comprising:

(a) a support frame;

(b) a fixture mounted on said support frame for holding at least one instrument with a predetermined site thereon in a preset position for grinding a predetermined surface at the predetermined site thereon;

(c) a grinding assembly mounted on said support frame and including a movable grinding belt having a planar span for grinding the predetermined surface at the predetermined site on the instrument;

(d) an oscillation producing mechanism mounted on said support frame and coupled to said fixture and being operable to oscillate said fixture and the instrument therewith relative to said grinding belt to reciprocally translate the predetermined site on the instrument substantially parallel and relative to said planar span of said grinding belt during said grinding of the predetermined surface at the predetermined site on the instrument by said movable grinding belt;

(e) a translation producing mechanism mounted on said support frame and supporting said grinding assembly and being operable to selectively translate said grinding assembly and thus said planar span of said grinding belt toward and away from the predetermined site on the instrument to permit receiving and setting up of the instrument in said fixture and to place the instrument in a position for said planar span of said grinding belt to grind the predetermined surface at the predetermined site on the instrument;

(f) a grinding angle setting mechanism mounted on said support frame and coupled to said grinding assembly and being operable to pivotally move said grinding assembly about a first pivot axis and thereby selectively change the angular relationship of said planar span of said grinding belt relative to the predetermined site on the instrument to grind another predetermined surface thereon; and (g) a grinding site setting mechanism mounted on said support frame and coupled to the instrument and being operable to rotate the instrument relative to said fixture and to said planar span of said grinding belt to selectively change the location of the predetermined site on the instrument.

16. The machine of claim 15 wherein said oscillation producing mechanism includes:

an auxiliary frame member supporting said fixture;

a support member mounted to said support frame and supporting said auxiliary frame member and thus said fixture therewith for undergoing translatory movement relative to said support frame along an axis extending substantially parallel to said planar span of said grinding belt; and drive means mounted to said support member and engaged with said auxiliary frame member for selectively driving said auxiliary frame member to reciprocally translate said fixture and thereby the predetermined site of the instrument held in said fixture in an oscillatory manner substantially parallel and relative to said planar span of said grinding belt.

17. The machine of claim 16 wherein said grinding site setting mechanism includes:

a guide track supported on said auxiliary frame member adjacent to said fixture also supported thereon;

rotary drive means for generating rotary motion; and movable means supported by said guide track adjacent to said fixture and said instrument held by said fixture, said movable means interconnecting said rotary drive means with the instrument for selectively rotating the instrument relative to said fixture and said planar span of said grinding belt to thereby selectively change the predetermined site on the instrument for grinding a predetermined surface at the predetermined site thereon.

18. The machine of claim 15 wherein said grinding assembly includes:

a support member mounted for undergoing pivotal movement about a first pivotal axis aligned with the preset position;

an auxiliary frame mounted to said support member and supporting said grinding belt for movement about an endless path;

a belt support platen mounted to said auxiliary frame adjacent to said fixture and along said endless path underlying said grinding belt so as to support a short section thereof extending along said fixture and engaged by the instrument in a planar orientation defining said planar span of said grinding belt intersecting said first pivotal axis of said support member and said preset position to grind the predetermined surface at the predetermined site on the instrument; and belt drive means mounted to said auxiliary frame and drivingly engaged with said grinding belt for driving said grinding belt about said endless path.

19. The machine of claim 18 wherein said translation producing mechanism includes:

a first supplementary frame member supporting said support member of said grinding assembly for undergoing pivotal movement about said pivotal axis aligned with the preset position;

a second supplementary frame member mounted to said support frame and supporting said first supplementary frame member for undergoing translatory movement relative to said support frame along a translatory axis extending in orthogonal relation to said pivotal axis; and translatory drive means mounted to said support frame and engaged with said first supplementary frame member for selectively driving said first supplementary frame member along said translatory axis and thereby translating said grinding assembly and said planar span of said grinding belt therewith toward and away from the predetermined site on the instrument.

20. The machine of claim 19 wherein said grinding angle setting mechanism includes:

a first auxiliary support member connected to said first supplementary frame member of said translation producing mechanism for undergoing pivotal movement relative thereto about a lower axis spaced from and aligned parallel with said pivot axis;

a second auxiliary support member connected to said first supplementary frame member for undergoing pivotal movement about an upper axis spaced from and aligned parallel with said lower and pivot axes; and drive means mounted to said first auxiliary support member and engaged with said second auxiliary support member for selectively driving said second auxiliary support member along a translation axis to thereby translate said second auxiliary support member toward and away from said first auxiliary support member and thereby selectively changing the angular relationship of said planar span of said grinding belt relative to the predetermined site on the instrument.

21. A belt grinding method for forming cutting edges of complex geometry on surgical instruments, said method comprising the steps of:

(a) holding at least one instrument with a predetermined site thereon in a preset position for grinding a predetermined surface thereon;

(b) operating a grinding belt having a planar span to grind the predetermined surface at the predetermined site on the instrument;

(c) oscillating the instrument and thus the predetermined site thereon substantially parallel and relative to the planar span of the grinding belt during the grinding of the predetermined surface at the predetermined site on the instrument by operating the grinding belt; and (d) selectively translating the grinding belt and thus the planar span therewith toward and away from the predetermined site on the instrument to permit receiving and setting up of the instrument in an instrument holding fixture and to place the instrument in a position for the planar span of the grinding belt to grind the predetermined surface at the predetermined site on the instrument.

22. The method of claim 21 further comprising the step of:

(e) selectively changing the angular relationship of the planar span of the grinding belt relative to the predetermined site on the instrument to grind another predetermined surface thereon.

23. The method of claim 21 further comprising:

(e) rotating the instrument relative to the planar span of the grinding belt for selectively changing the location of the predetermined site on the instrument.

24. A belt grinding method for forming cutting edges of complex geometry on surgical instruments, said method comprising the steps of:

(a) holding at least one instrument with a predetermined site thereon in a preset position for grinding a predetermined surface thereon;

(b) operating a grinding belt having a planar span to grind the predetermined surface at the predetermined site on the instrument; and (c) selectively translating the grinding belt and thus the planar span therewith toward and away from the predetermined site on the instrument to permit receiving and setting up of the instrument in an instrument holding fixture and to place the instrument in a position for the planar span of the grinding belt to grind the predetermined surface at the predetermined site on the instrument.

25. The method of claim 24 further comprising the step of:

(d) selectively changing the angular relationship of the planar span of the grinding belt relative to the predetermined site on the instrument to grind another predetermined surface thereon.

26. The method of claim 24 further comprising:

(d) rotating the instrument relative to the planar span of the grinding belt for selectively changing the location of the predetermined site on the instrument.

27. A belt grinding method for forming cutting edges of complex geometry on surgical instruments, said method comprising the steps of:

(a) holding at least one instrument with a predetermined site thereon in a preset position for grinding a predetermined surface thereon;

(b) operating a grinding belt having a planar span to grind the predetermined surface at the predetermined site on the instrument;

(c) selectively changing the angular relationship of the planar span of the grinding belt relative to the predetermined site on the instrument to grind another predetermined surface thereon;

(d) rotating the instrument relative to the planar span of the grinding belt for selectively changing the location of the predetermined site on the instrument; and (e) selectively translating the grinding belt and thus the planar span therewith toward and away from the predetermined site on the instrument to permit receiving and setting up of the instrument in an instrument holding fixture and to place the instrument in a position for the planar span of the grinding belt to grind the predetermined surface at the predetermined site on the instrument.

28. The method of claim 27 further comprising the step of:

(f) oscillating the instrument and thus the predetermined site thereon substantially parallel and relative to the planar span of the grinding belt concurrently with grinding of the predetermined surface at the predetermined site on the instrument.

* * * * *